United States Patent [19]

Buma

[11] Patent Number: 5,374,254

[45] Date of Patent: Dec. 20, 1994

[54] CATHETERS WITH ADJUSTABLE EXTERNAL LOCKING BOLSTERS

[76] Inventor: Shelley J. Buma, 218 Hill St., Whitinsville, Mass. 01588

[21] Appl. No.: 845,163

[22] Filed: Mar. 3, 1992

Related U.S. Application Data

[63] Continuation-in-part of Ser. No. 619,762, Nov. 29, 1990, Pat. No. 5,092,850.

[51] Int. Cl.$^5$ ............................................. A61M 5/32
[52] U.S. Cl. .................... 604/175; 609/178; 609/256; 609/283; 609/284
[58] Field of Search .................. 128/DIG. 26, 207.17, 128/200.26, 912; 604/104, 164, 174, 175, 178, 179, 167, 905, 256, 283, 284, 106, 105

[56] References Cited

U.S. PATENT DOCUMENTS

| | | | |
|---|---|---|---|
| 3,241,554 | 3/1966 | Coanda | 128/DIG. 26 |
| 4,393,873 | 7/1983 | Nawash et al. | 128/DIG. 26 |
| 4,578,068 | 3/1986 | Imman et al. | 604/175 |
| 4,645,492 | 2/1987 | Weeks | 128/DIG. 26 |
| 4,834,712 | 5/1989 | Quinn et al. | 128/DIG. 26 |
| 4,944,732 | 7/1990 | Russo | 604/175 |
| 4,995,868 | 2/1991 | Brazier | 604/105 |
| 5,041,085 | 8/1991 | Osborne et al. | 604/178 |
| 5,073,166 | 12/1991 | Parks et al. | 604/105 |
| 5,092,850 | 3/1992 | Buma | 604/178 |
| 5,125,847 | 6/1992 | Quinn et al. | 604/175 |

FOREIGN PATENT DOCUMENTS 0373366  5/1907  France ..................... 604/106

OTHER PUBLICATIONS

Redo et al, "A Stainless Steel Cannula for the Creation of Gastrointestinal Fistulas", 1954, 4 pages.

Primary Examiner—Randall L. Green
Assistant Examiner—K. M. Reichle
Attorney, Agent, or Firm—Woodard, Emhardt, Naughton, Moriarty & McNett

[57] ABSTRACT

Medical devices are disclosed which are adapted for indwelling placement in a patient. In one device, a flexible tubular catheter is adapted for placement with its distal end inside of the body and its proximal end outside of the body, and defines a lumen which provides a fluid passageway between its proximal and distal ends. The flexible tubular member has multiple engagement elements located on its outside surface, and an external bolster is provided which includes multiple engagement elements complementary to the engagement elements located on the tubular catheter for adjustably coupling the bolster and the tubular catheter. After placement, the bolster locks to the tubular member such that the bolster can rest securely close to the skin surface. In a first disclosed embodiment, a compression element locks the bolster to the tubular member after selective positioning of the bolster onto the tubular member. In a second embodiment, the bolster has a curved passageway which opens to a side port, and the bolster lumen has engagement elements about the curved passageway which are complementary to the engagement elements located on the tubular member. The bolster is locked into position by the tension between engaged engagement elements caused by the bending of the flexible tubular member in the curved passageway within the side-port bolster. In this way, the bolster is capable of being selectively positioned and locked onto the tubular member to allow the bolster to rest closely to the skin surface without requiring an additional compression element.

16 Claims, 5 Drawing Sheets

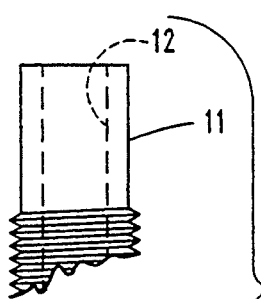
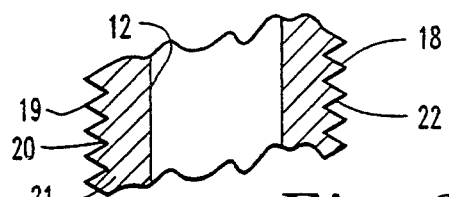
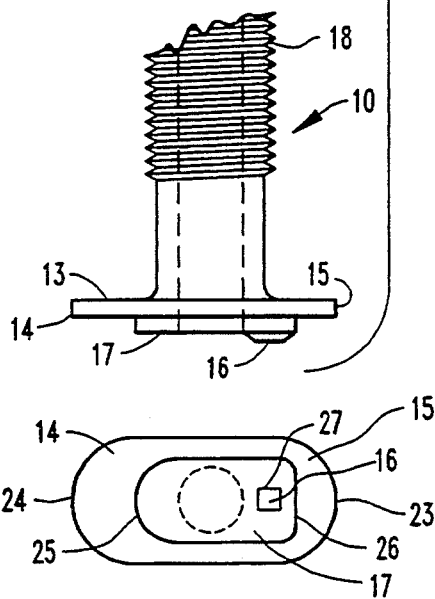
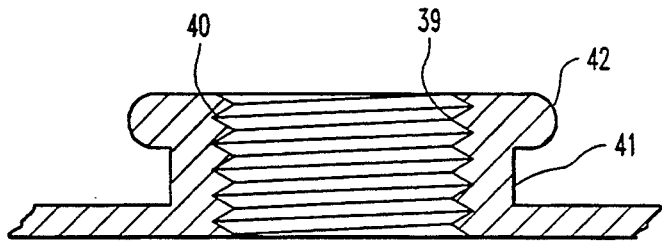
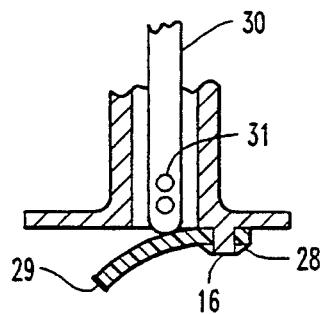
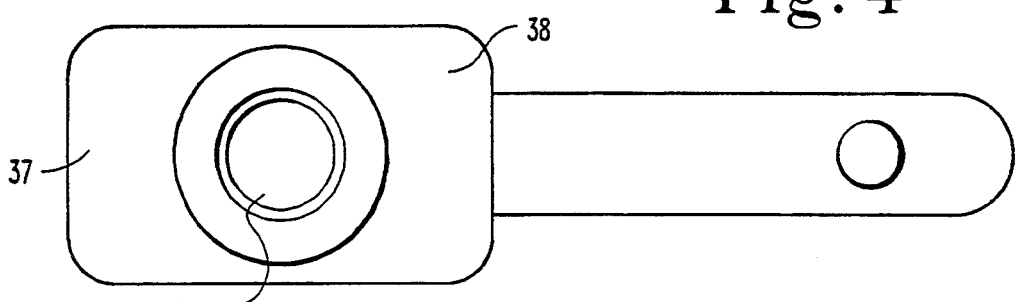
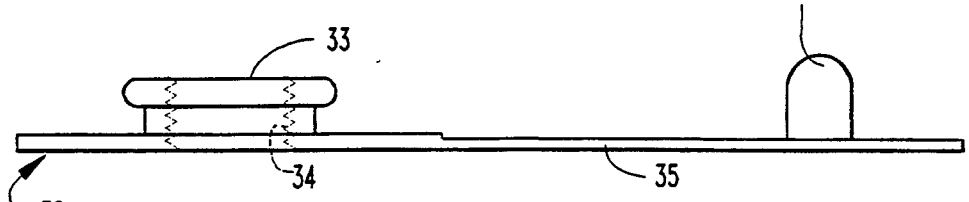

Fig. 15
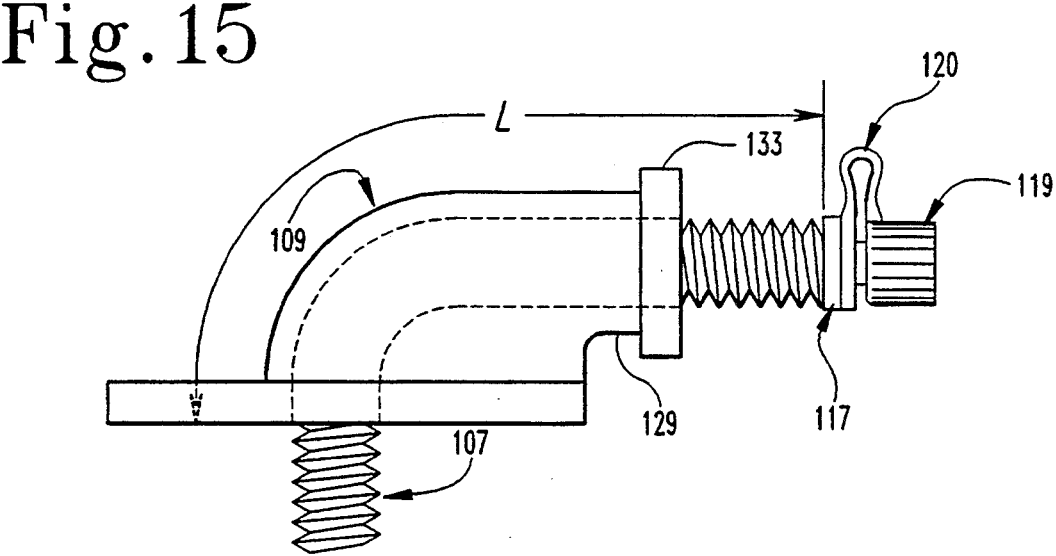
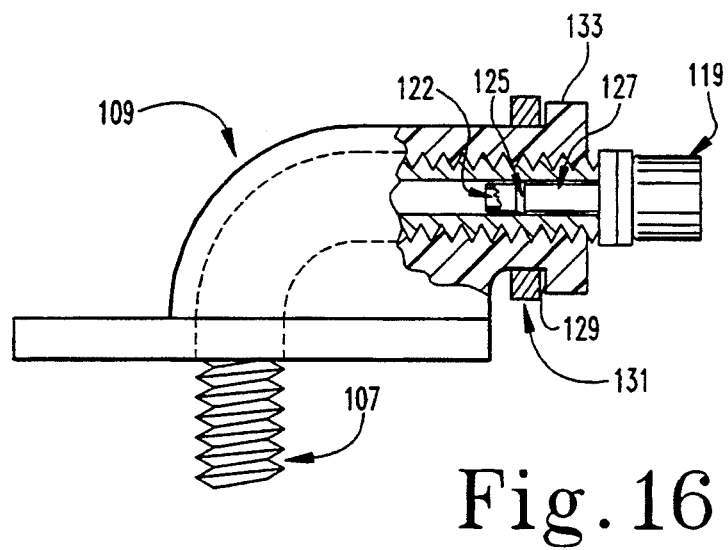
Fig. 16
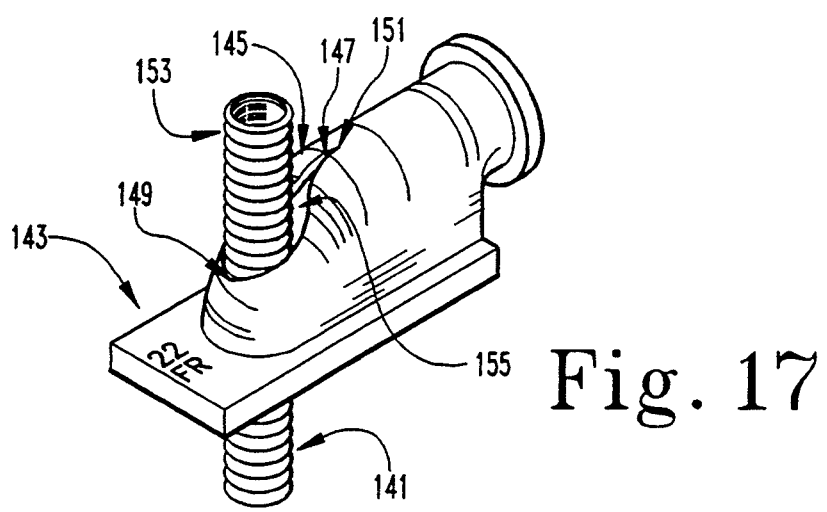
Fig. 17

CATHETERS WITH ADJUSTABLE EXTERNAL LOCKING BOLSTERS

REFERENCE TO RELATED APPLICATIONS

This application is a continuation-in-part of United States patent application Ser. No. 07/619,762, filed on Nov. 29, 1990, by the same inventive entity, and entitled CATHETER WITH ADJUSTABLE EXTERNAL LOCKING BOLSTER, now U.S. Pat. No. 5,092,850 which issued Mar. 3, 1992.

BACKGROUND OF THE INVENTION

The use of various indwelling catheters, especially feeding devices, is well known in the medical art. Feeding tubes may be left in place within the body for a considerable period of time, often up to a year. This is possible due to the use of recent advancements in biocompatible materials, especially silicone indwelling devices which permit long term placement of a device without body rejection or tissue reaction. Medical grade silicone devices are routinely used in gastrostomy feeding devices as well as other types of devices such as wound drains and infusion catheters. The silicone material has many biocompatibility advantages including the ability to remain soft and flexible for long periods of time within the body.

Feeding devices and catheters made from silicone are molded, extruded, and assembled such that the silicone material is very smooth and the surface finish has a very low coefficient of friction. The surface of the silicone catheter becomes very slippery especially when it is in contact with body fluids. As a result, these devices have displayed a tendency to migrate after they have been implanted. To prevent inward migration, designers and manufacturers have added external retention devices to their products. Silicone retention discs are manufactured in various sizes to stabilize catheters and are produced by such companies as Wilson-Cook. Low profile gastrostomy ports of fixed length are also are available in various sizes and lengths with integrally molded bolsters incorporated therein to prevent tube migration.

Retention discs may easily slide on the tubular shaft of the catheter allowing the migration of the catheter into the body. If the catheter slips a sufficient distance this may allow an inner balloon to cause an obstruction or require adjustment of the device. Pull ties have been added to these discs to prevent disc slippage, however, the disc can still fail even with the pull tie in place, due to the smooth slippery outer surface of the catheter and the smooth inner surface of the molded retention disc.

Gastrostomy devices commonly are supplied in various fixed lengths to accommodate differing lengths of stoma tract. Gauderer U.S. Pat. No. 4,803,438, and Russo U.S. Pat. No. 4,944,732, disclose examples of low profile devices that are supplied in various fixed lengths for this purpose. Patients, however, cannot be fitted with a fixed length device when the correct length is not available. Therefore, a large inventory of these devices in a variety of fixed lengths and sizes needs to be maintained at a considerable added expense. This type of device also requires additional equipment to measure the lengths of patients' stoma tracts to determine appropriate sizing for placement. These disadvantages have limited the usefulness for such low profile devices.

SUMMARY OF THE INVENTION

The present invention provides new and unique gastrostomy devices with adjustable external bolsters to prevent inward tube migration that can be easily and securely locked into place to eliminate tube slippage. The disclosed embodiments include means for locking the bolster to the tubular member to allow the bolster to be selectively positioned and locked onto the tubular member such that the bolster can rest securely close to the skin surface.

In one embodiment, a flexible tubular catheter is adapted for placement with its distal end inside of the body and its proximal end outside of the body, and defines a lumen which provides a fluid passageway between its proximal and distal ends. The flexible tubular member has multiple engagement elements located on its outside surface, and an external bolster is provided which includes at least one engagement element complementary to the engagement elements located on the tubular catheter for adjustably coupling the bolster and the tubular catheter. A compression element locks the bolster to the tubular member after selective positioning of the bolster onto the tubular member, with the bolster resting securely close to the skin surface.

In a second embodiment, a bolster with a side exit port is provided with an alternative approach for locking onto the catheter. A side-port bolster has a curved passageway which opens to a side port and engagement elements about the curved passageway which are complementary to the engagement elements located on the tubular member. Engagement elements are located on both the vertically oriented portion of the curved passageway and the side oriented portion thereof. The bolster is locked into position by the tension between engaged engagement elements of the catheter and the side-oriented engagement elements of the bolster caused by the bending of the flexible tubular member into the curved passageway within the side-port bolster.

Accordingly, it is a primary objective to provide a device which is safer, more convenient to use, and less expensive than the devices presently manufactured.

It is a further objective to provide an external bolster which can be easily positioned by the physician, and which can be easily and securely locked into place after being so positioned.

Another objective is to have the bolster, after locking it in place, become unitized on the catheter such that the catheter cannot move inward inside the body.

Another important objective is to provide a low profile, close to the skin surface catheter device which is adjustable in length to fit a wide range of lengths of stoma tract, thus eliminating the need for stoma tract length measuring devices in low profile gastrostomy feeding ports.

Another important objective is to provide a low profile, close to the skin surface gastrostomy device which can be placed for the first time in a patient using the percutaneous endoscopic gastrostomy technique.

Another objective is to provide a replacement low profile, close to the skin surface gastrostomy device which can be easily inserted and adjusted to the stoma tract length.

Another objective is to permit the use of a plug-in rigid plastic feeding adapter with closure cap with the bolster. A further objective is to eliminate the requirement of internal anti-reflux valves and thereby eliminate the need for separate decompression tubes.

A further objective of the present invention is to provide a side exit device which meets the above stated objects.

A yet further objective is to secure the catheter to the bolster without the need for a separate compression element.

These and other objects and advantages of the present invention will become apparent from a review of the following specification and claims.

BRIEF DESCRIPTION OF THE DRAWINGS

FIG. 1 is a partial side view of a tubular catheter including engagement elements on its outside diameter, and a flexible tip with an anti-reflux valve shown normally closed.

FIG. 2 is an enlarged partial sectional view of the engagement elements shown in FIG. 1.

FIG. 3 is an underside view of the catheter of FIGS. 1-2, showing its flexible tip with anti-reflux valve.

FIG. 4 is a partial sectional side view of distal tip of the catheter of FIGS. 1-3, with its anti-reflux valve being shown opened by a rounded tip drainage catheter.

FIG. 5 is a side view of an external top-port bolster showing internal engagement elements and a closure cap.

FIG. 6 is a top view of the external top-port bolster of FIG. 5.

FIG. 7 is a partial sectional enlarged view of the bolster of FIGS. 5-6, showing the internal engagement elements located therein.

FIG. 15 is a side view of a side-port bolster and catheter having an adapter plugged into the catheter outside the bolster.

FIG. 16 is a partial cross section of the side-pod bolster, catheter, and adapter assembly of FIG. 15 having the proximal end of the adapter positioned inside the bolster including the added security of a compression element.

FIG. 17 is an isometric view of a side-pod bolster with a pre-slit top permitting the catheter to be positioned vertically inside the bolster to provide a top-port.

DESCRIPTION OF THE PREFERRED EMBODIMENT

Figure 8:
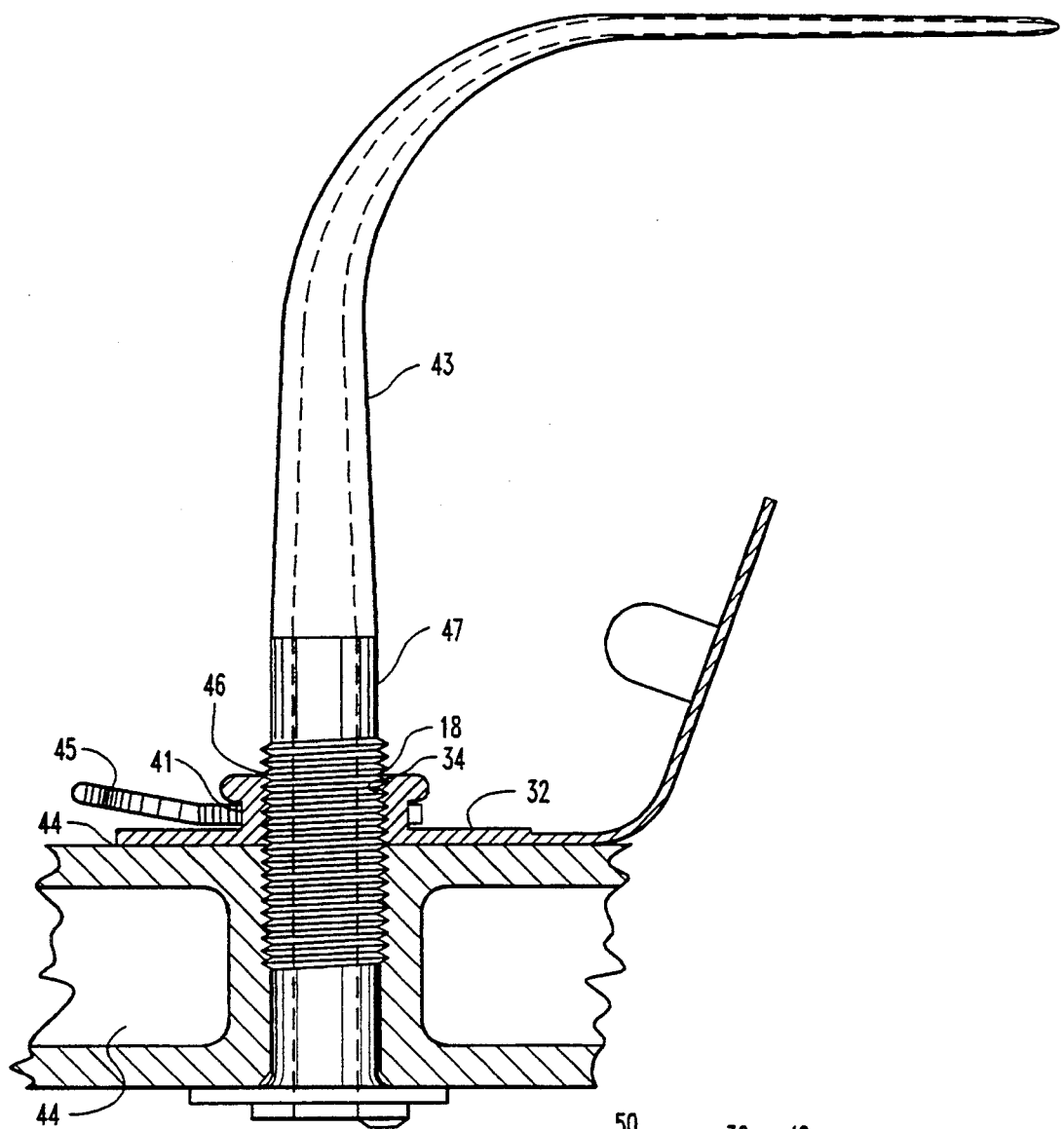
FIG. 8 is a sectional view of a catheter after placement in a body cavity showing it pre-assembled to a dilator, with the external bolster of FIGS. 5-7 adjusted down close to the skin surface and a compression pull tie securing the engagement elements of the catheter and bolster together.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated devices, and such further applications of the principles of the invention as illustrated therein being contemplated as would normally occur to one skilled in the art to which the invention relates.

A first embodiment of the present invention will now be described with reference to FIGS. 1-9. FIG. 1 shows a molded catheter 10 which is tubular in shape with outside wall 11 and inside lumen 12. Lumen 12 extends the full length of the catheter. Catheter 10 can be molded from medical grade silicone either by compression or the liquid injection molding process. A small percentage, about 5%, of Barium can be formulated within the silicone to make the device radiopaque.

Distal tip 13 is integrally molded as pad of tubular catheter 10. Tip 13 has outwardly extending flanges 14 and 15. Protruding downward and molded into tip 13 is square-shaped lug 16. Separately silicone molded anti-reflux valve 17 is of the flapper-type.

Externally molded onto the outside wall 11 of catheter 10 is a series of saw tooth rings 18 which are molded around the entire circumference of outside wall 11. Saw tooth rings 18 should begin within ½ inch of the distal tip and extend proximally along the catheter for a length of at least 3 inches.

FIG. 2 is an enlarged sectional view of saw tooth rings 18. The crest 19 of the tooth is the same dimension for all crested teeth. The valley 20 of the tooth is also the same dimension for all valleyed portions of the teeth. The width of the tooth at its base 21 is about 0.050 inches and the height of each tooth from valley to crest is also 0.050 inches. Inside lumen 12 is molded smooth.

FIG. 3, which shows the underside of distal tip 13, shows flanges 14 and 15 with rounded edges 23 and 24. Anti-reflux flapper valve 17 is molded flat with a rounded forward edge 25 and rearward straight edge 26. A square shaped hole 27 is molded into valve 17 to mate with lug 16.

FIG. 4 shows lug 16 extending slightly beyond the valve surface so that liquid silicone adhesive 28 can adhesively bond lug 16 to valve 17. Lug 16 both positions and correctly aligns the valve in place and acts as an adhesive lug. The rounded edge 25 is free to flap open as in 29. A hollow drainage obturator 30 which is semi-rigid, and extruded and molded of PVC plastic can easily open flap valve 17 to drain or decompress a body cavity. Side drainage holes 31 can be positioned at the obturator tip.

FIG. 5 shows a side view of external bolster 32 which is also molded of silicone rubber. Bolster 32 has an opening 33 molded therein with internal saw teeth rings 34 which match external saw teeth rings 18 on tubular shaft of catheter 10. Extending off to one side of bolster 32 is a molded-in strap 35 with a male closure plug 36. FIG. 6 is a top view of the bolster 32 showing outward flanges 37 and 38.

FIG. 7 is an enlarged partial sectional view of bolster 32, showing the internal engagement elements therein. Internally molded saw teeth have crests 39 and valleys 40 which correspond to crests 19 and valleys 20 as shown in FIG. 2. The body of bolster 32 has a recessed groove 41 which runs around the entire outside surface of bolster 32. Above groove 41 is a collar 42.

FIG. 8 shows catheter 10 after placement within the body. If to be used as a gastrostomy feeding device, catheter 10 can be placed using the standard percutaneous endoscopic technique using either the "push" method or the "pull" method. Attached to the proximal end of catheter 10 is a long tapered dilator 43 which facilitates placement using the endoscopic technique. The catheter is placed through the stomach wall 44'. Bolster 32 is slid over dilator 43 and ratchets down over saw teeth 18 on the catheter shaft.

Matching internal saw teeth 34 engage with saw teeth 18. In practice, external bolster 32 can ratchet down 0.050 inches at a time for an precise fit down to skin surface 44. Flanges 37 and 38 on the bolster can rest gently on the skin surface 44. If bolster 32 is too tight down on the skin surface, it can be retracted upward by grasping and pulling collar 42. In this way, bolster 32 can be adjustable in either upward or downward movement on the tubular shaft in precise increments.

Once in position, bolster 32 can be secured by placing nylon pull tie 45 into groove 41 and compressing it securely about bolster 32. Pull tie 45 compresses internal saw teeth 34 on bolster 32 to lock with matching teeth 18 on catheter 10, Once compressed, the crests and valleys of teeth 18 and 34 cannot move out position and bolster 32 is thus securely locked onto catheter 10. Pull tie 45 is of the one-way compression engagement nylon molded type. Once pulled tight, it cannot be retracted. After securing pull tie 45, catheter 10 is carefully trimmed at surface 46 to remove excess tube 47 and dilator 43.

Figure 9:
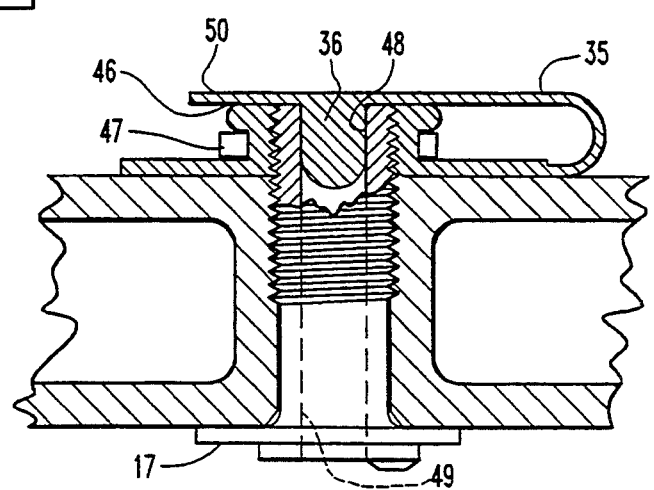
FIG. 9 is a sectional view of the catheter and bolster of FIG. 8 in a body cavity after the dilator and compression pull tie have been trimmed away, with the closure cap in place with the device shown in a low profile, close to the skin surface mode.

FIG. 9 shows a cross sectional view of the device in its final form after placement and in its low profile, close to the skin surface look. After trimming catheter surface 46, pull tie 45 is also trimmed back to point 47 for a neat appearance. The catheter lumen is fully open at point 48 and extends the full length to outward opening 49 at the distal tip. Closure plug 36 will fit directly into lumen 12 at point 48. Plug 36 can be opened by pulling on tab 50 on the strap 35. The device now becomes a complete, easy to place, low profile, close to the skin surface portal device.

The above described catheter can be attached to arty desired administration set for the delivery of feeding formula or medications. The anti-reflux valve 17 permits one-way infusion into the device, but prevents body fluids front escaping. Valve 17 can be opened at anytime to drain the device by opening cap 36 and inserting drainage tube 30.

Some physicians prefer other style distal tips such as pezzer type, conical type, mushroom type, or malecot type. These are all hollow bulbous types of tips which are deformable to be inserted or placed inside a body cavity, particularly the stomach. Rigid obturators are used to stretch out these tips during insertion. Anti-reflux valves can be incorporated in any one of these alternate style tips, and the device can readily be designed with any of these tips in mind.

As can be be seen from FIG. 9 the device in its final form is a very low profile, close to the skin surface device. Ease of placement, patient comfort, low cost, and the ability for the patient to lead a normal active life, are all advantages of this device.

Referring now to FIGS. 10-17, a second embodiment is illustrated which incorporates a bolster with a side exiting port and utilizing an alternative approach for locking onto a catheter. Side-port bolster 51 is used to orient a catheter port from a vertical to a side position. It is contemplated that this side-pond device includes the features disclosed in FIGS. 1-9 for the top-port device and includes additional features, as described below. Bolster 51 has a port-side 59 and a flange-side 61, and includes flange 55 and wall 57. Bolster 51 also has a bolster lumen 63 defined by wall 57 which provides a bolster passageway 65 between the flange-side 61 and the port-side 59 that is adapted for insertion of the proximal end of a catheter (See FIG. 13).

Figure 13:
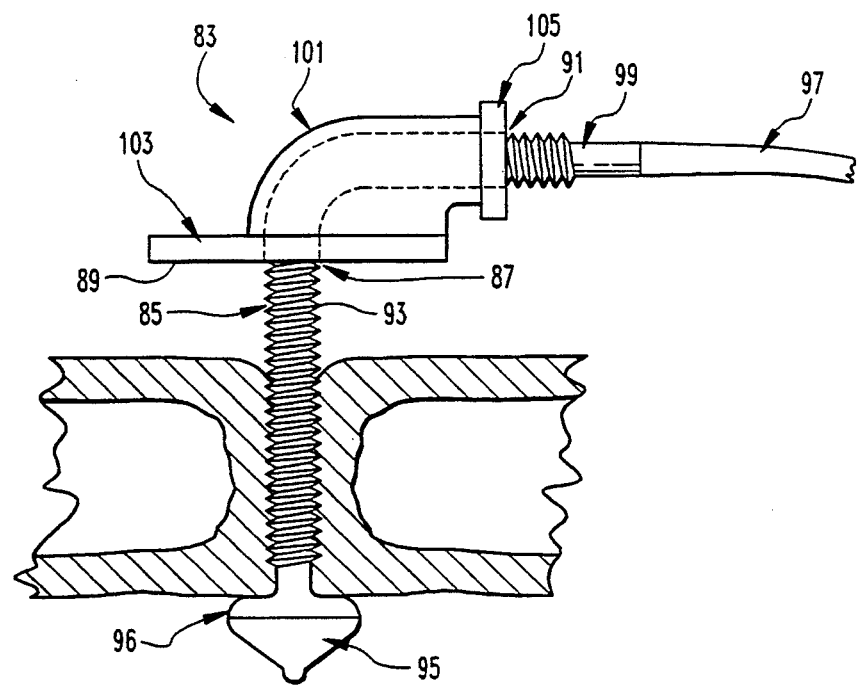
FIG. 13 is a side view of a side-port bolster slidably positioned on a first time gastrostomy catheter with dilator.

Bolster 51 further comprises flange-side engagement elements 66 located nearby the flange-side 61 in bolster passageway 65 for adjustably coupling bolster 51 to a catheter. Flange-side engagement elements 66 are complementary to engagement elements located on catheter 85 and include crests 67 and valleys 68 similar to those shown in FIGS. 1, 2 and 7, and are in aligned orientation relative to the normal implanted orientation of catheter 85. The complementary crests and valleys engage to couple bolster 51 to catheter 85, as shown in FIG. 13.

Side oriented port-side engagement elements 69 are an additional feature associated with side-port bolster 51 which assist in the locking of bolster 51 to a tubular member. Passageway 65 includes a curve 71 between the flange-side 61 and the pod-side 59. Side oriented port-side engagement elements 69 are located in passageway 65 near the pod-side 59 and are complementary to engagement elements 93 of catheter 85 (See FIG. 13). Side oriented pod-side engagement elements 69, however, are in non-aligned orientation relative to the normal implanted orientation of catheter 85 and, due to this relative orientation, provide in conjunction with the normal orientation and flexibility of catheter 85, for the secure locking of bolster 51 onto catheter 85 without the need for a separate compression element. This is accomplished because bolster 51 is lockable into position by the tension between side oriented engagement elements 69 and engagement elements 93 of catheter 85 caused by the bending of the flexible catheter 85 in curved passageway 65 within side-port bolster 51. In this way, bolster 51 is capable of being selectively positioned and locked onto the tubular member to allow flange 55 to rest closely to the skin surface, without the need for additional securing means.

An exterior curved shoulder 73 corresponds to the curve 71 in the passageway 65. Shoulder 73 includes a slit 75 as means for passing the proximal end of the catheter therethrough rather than through the pod-side of the passageway thereby allowing a top-pod arrangement if the physician so desires.

A compression element may additionally be placed about bolster 51 for additional security in locking an adapter to the proximal end of the catheter. If a compression element is desired, it may be placed in recess groove 77 near collar 79. Flange 55 may optionally include a marking 81 molded into the flange corresponding to the French catheter size of the bolster passageway 65 for easier selection of the appropriate sized bolster for the catheter.

The entire assembly for the side-pod bolster is designed to offer all the advantages of the top-pod device shown in FIGS. 5-9 yet provide added security, and a positive leak proof LUER-LOCK connector for long term use of the device. It is preferred that the side-pod bolster be molded in one piece of silicone medical grade rubber or injection molded from a soft flexible synthetic rubber such as KRATON although alternative methods and materials for construction are contemplated. It is further contemplated that the engagement elements in the bolster comprise saw-tooth ring type moldings which mate with complementary saw-tooth type rings comprising the catheter engagement elements described above. Whereas the flat bolster of FIGS. 5-9 is raised from the abdominal skin surface about 1 centimeter, the side-pod bolster of FIGS. 10-17 is raised about 1½ centimeters.

Figure 10:
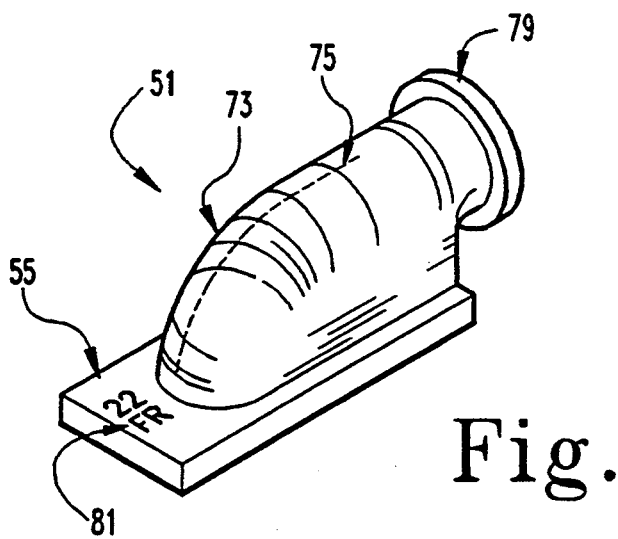
FIG. 10 is an isometric view of a side-pod bolster.
Figure 11:
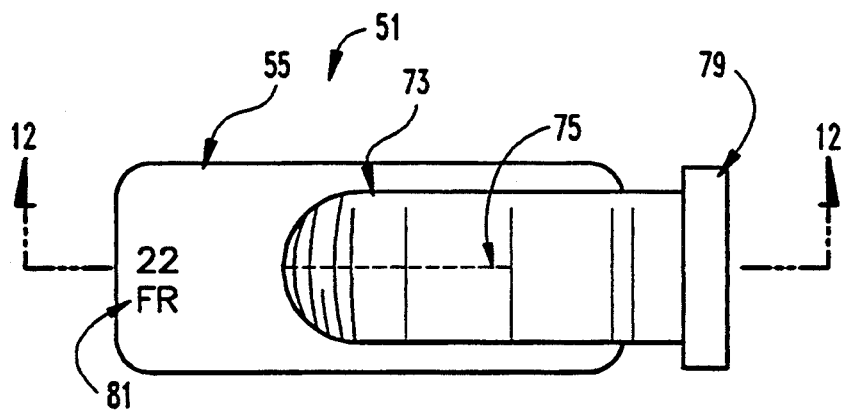
FIG. 11 is a top view of the side-pod bolster of FIG. 10.
Figure 12:
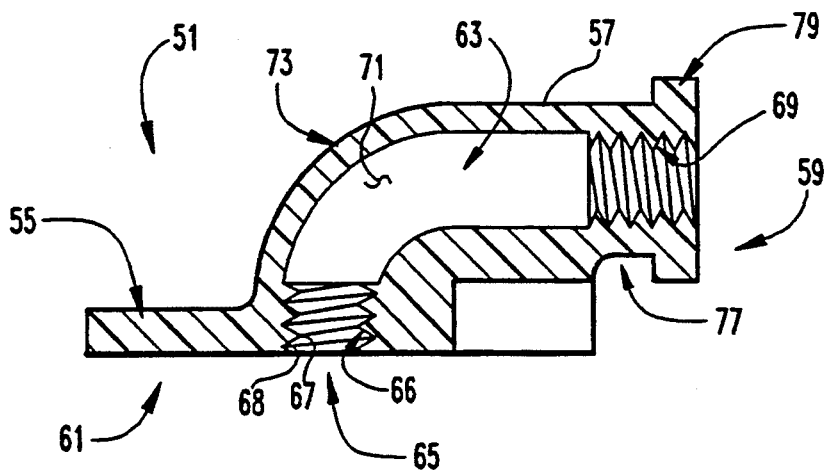
FIG. 12 is a cross-sectional side view of the side-pod bolster of FIGS. 10-11 taken along lines 12—12 in FIG. 11.

FIG. 13 illustrates a side-pod bolster 83 of the same construction as bolster 51 in FIGS. 10-12, positioned on a first-time tubular gastrostomy catheter 85 in preparation for indwelling placement into the body. A portion of the body is shown in cross section to illustrate the proper orientation of the device. Catheter 85 enters bolster 83 through passageway 87 at its flange-side 89 and exits passageway 87 at the port-side 91 of bolster 83. Bolster 83 can be slidably positioned on catheter 85 to allow its flange-side 89 to rest closely to the skin surface.

Catheter 85 includes engagement elements 93 complementary to engagement elements located in passageway 87 (See FIG. 12). Catheter 85 also includes tip 95 at its distal end 96 which is placed inside the body and dilator 97 attached to its proximal end 99. Also shown are shoulder 101, flange 103 and collar 105.

Figure 14:
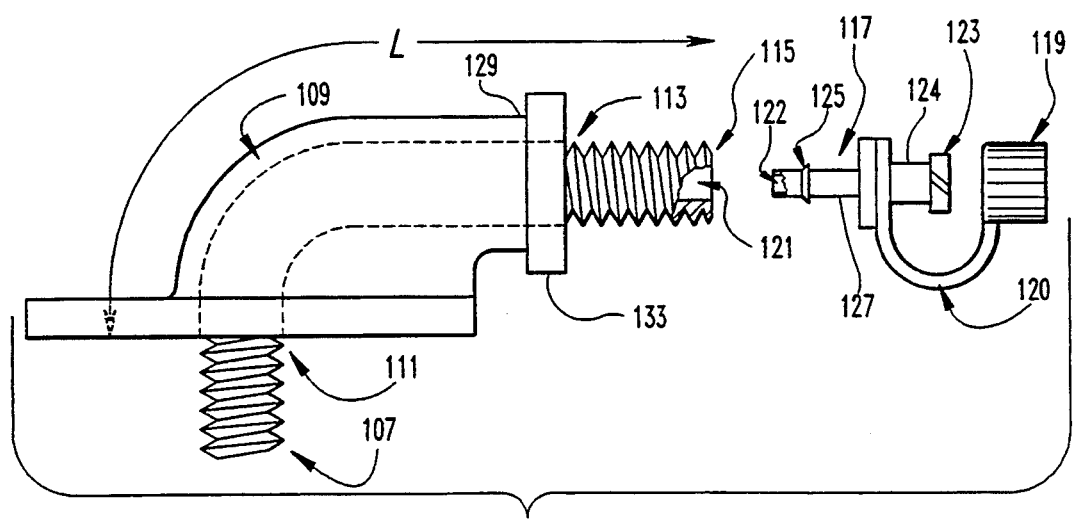
FIG. 14 is a partial side view of the side-port bolster of FIG. 13 on a catheter which has been cut after placement to a fixed length and a plug in feeding adapter ready for insertion into the catheter lumen.

Referring to FIGS. 14-16, side-port bolster 109 and catheter 107 are shown with a complementary external adapter. Bolster 109 includes the features of bolsters 51 and 83 in FIGS. 10-13 and catheter 107 includes the same features as catheter 85 of FIG. 13. FIG. 14 illustrates catheter 107 extending through bolster 109 from the flange end 111 through the port end 113, and catheter 107 has been trimmed at point 115 to provide a length L extending from the body after placement. In this embodiment, length L is about three centimeters. A plug-in feeding adapter 117 is also shown prior to attachment to catheter 107. A template (not shown) can be provided to aid in the determination of the exact length of the catheter that should extend outside of the body.

Once catheter 107 has been placed and cut to the desired length L, plug-in feeding adapter 117 with closure cap 119 and tethered strap 120 can be directly plugged into catheter lumen 121, shown in partial cross-section in FIG. 14. Feeding adapter 117 also includes a continuous lumen 122, also shown in partial cross-section in FIG. 14, a female LUER-LOCK type connection 123 at its proximal end 124, and an engagement element 125 located on its distal end 127 for engaging the catheter as the distal end is inserted into the catheter lumen 121. The female LUER-LOCK type connection 123 is especially preferred because it provides a tight fitting leak proof connection for attachment of an administration set (not shown) which may be used to deliver medication or enteral formula.

FIGS. 15 and 16 show catheter 107, bolster 109 and plug-in feeding adapter 117 assembled for patient use. FIG. 15 also shows the length of catheter the body L, which is about three centimeters. Once adapter 117 is plugged into catheter lumen 121, catheter 107 is additionally secured from slippage back into the body because the distal end 127 of adapter 117 expands the catheter diameter thereby preventing inward migration of the tube.

FIG. 16 illustrates a partial sectional view of a preferred orientation after placement of the catheter 107, bolster 109 and adapter 117. Catheter 107 is shown cut about one half centimeter shorter than in FIG. 15 to allow distal end 127 to extend further into bolster 109 to allow engagement element 125 to extend past groove 129 near collar 133. Groove 129 is positioned between engagement element 125 and proximal end 124. Compression element 131 such as a pull tie can be placed into groove 129 to lock catheter 107, bolster 109, and adapter 117 together. The assembly of either FIG. 15 or FIG. 16 provides a compact side-ported low profile entrance pod for accessing any interior body cavity, vein, or artery.

FIG. 17 illustrates a catheter 141 and a bolster 143 having a shoulder 145 and a slit 147 to allow the side-pod bolster to include a top-pod conformation. Bolster 143 includes the features of bolsters 51, 83 and 109 in FIGS. 10-16. Shoulder 145 corresponds externally to a curve in the passageway and includes slit 147 which extends from point 149 to point 151 to allow the passage of the proximal end 153 therethrough (See FIG. 12). Slit 147 provides access to passageway 155 to allow catheter 141 to exit through shoulder 145 to allow an alternative top-port conformation for the side-pod bolster. Bolster 143 may be provided with a line as a guide for placement of a slit therein or may be supplied pre-slit. The alternative top-port orientation can be especially useful when the device is replacing a device having a top-pod.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A medical device adapted for indwelling placement in a patient comprising:
   a flexible tubular member having a proximal end and a distal end, wherein said distal end is adapted for placement inside of a body of the patient in a normal implanted orientation and said proximal end is adapted for placement outside of the body; said tubular member further defining a lumen which provides a fluid passageway between said proximal and said distal ends: said flexible tubular member further having multiple engagement elements located on an outside surface;
   a separate external coupling incorporating at least one matching engagement element capable of selective engagement with at least one of said multiple engagement elements on the outside surface of said tubular member to selectively position said coupling on said tubular member such that said coupling rests close to a skin surface outside the body;
   means for locking said coupling to said tubular member after selective positioning of said coupling on said tubular member to rest securely close to the skin surface to prevent said engaged engagement elements on both said coupling and said tubular member from disengagement such that said coupling and tubular member become fixed together to prevent inward migration of the tubular member within the body and wherein said coupling defines a curved passageway having a proximal end and a distal end and said coupling includes multiple matching engagement elements positioned within said curved passageway including at least one aligned-oriented engagement element in the distal end of said curved passageway which defines means for selective engagement with at least one of said multiple engagement elements on the outside surface of said tubular member in an aligned orientation relative to the normal implanted orientation and at least one side-oriented engagement element in the proximal end of said curved passageway which defines means for selective engagement with at least one of said multiple engagement elements on the outside surface of said tubular member in a non-aligned orientation relative to the normal implanted orientation and wherein said locking means includes tension between at least one of said engaged engagement elements of said tubular member with said at least one side-oriented engagement element of said coupling caused by bending of said flexible tubular member within said curved passageway.

2. The device of claim 1, wherein said engagement elements on both said coupling and said tubular member are a series of saw tooth rings.

3. The device of claim 1 wherein said means for locking said coupling to said tubular member further includes a compression element capable of locking said coupling to said tubular member after selective positioning of said coupling on said tubular member and wherein said compression element prevents slippage of said coupling from said tubular member.

4. The device of claim 3 further comprising a groove and a collar on said coupling, and wherein said compression element is located about said groove such that said coupling and said tubular member cannot be disengaged without relieving said compression element.

5. The device of claim 4, wherein said compression element is a pull tie.

6. The device of claim 1, further comprising an exterior shoulder on said coupling corresponding externally to said curved passageway, wherein said shoulder includes slit means for passing said proximal end of said tubular member therethrough.

7. The device of claim 1, wherein said distal end of said tubular member includes a deformable tip.

8. The device of claim 1, further comprising a plug-in feeding adapter attached to said tubular member.

9. The device of claim 8 wherein said adapter is secured with a compression element.

10. The device of claim 1, wherein an anti-reflux valve is provided on said tubular member to prevent reflux of fluid from exiting the passageway to the outside of the body.

11. The device of claim 1, wherein said coupling further includes means for compressed engagement to prevent inward migration of said tubular member.

12. The device of claim 11 wherein said means for compressed engagement includes a groove, a collar and a compression element located on said coupling, and wherein said coupling and said tubular member cannot be disengaged without relieving said compression element.

13. The device of claim 12 wherein said compression element is a pull tie.

14. The device of claim 1, wherein said distal end of said tubular member includes a distal tip which is flexible, hollow and capable of being inserted inside the body using a rigid obturator.

15. The device of claim 1, wherein said distal tip of said tubular member consists of at least one outwardly extending flange.

16. The device of claim 1, wherein said engagement elements on both said coupling and said tubular member are a series of complementary saw tooth rings.

* * * * *

UNITED STATES PATENT AND TRADEMARK OFFICE
CERTIFICATE OF CORRECTION

PATENT NO. : 5,374,254

DATED : December 20, 1994

INVENTOR(S) : Shelley J. Buma

Page 1 of 3

It is certified that error appears in the above-identified patent and that said Letters Patent is hereby corrected as shown below:

In column 3, line 45, please delete "side-pod" and insert in lieu thereof --side-port--.

In column 3, line 47, please delete "side-pod" and insert in lieu thereof --side-port--.

In column 3, line 61, please delete "side-pod" and insert in lieu thereof --side-port--.

In column 3, line 66, please delete "side-pod" and insert in lieu thereof --side-port--.

In column 4, line 24, please delete "pad" and insert in lieu thereof --part--.

In column 5, line 30, please insert --of-- between the words "out" and "position".

In column 5, line 48, please delete "arty" and insert in lieu thereof --any--.

In column 5, line 52, please delete "front" and insert in lieu thereof --from--.

In column 6, line 6, please delete "side-pond" and insert in lieu thereof --side-port--.

In column 6, line 30, please delete "pod-side", and insert in lieu thereof --port-side--.

In column 6, line 32, please delete "pod-side", and insert in lieu thereof --port-side--.

In column 6, line 34, please delete "pod-side", and insert in lieu thereof --port-side--.

UNITED STATES PATENT AND TRADEMARK OFFICE
CERTIFICATE OF CORRECTION

PATENT NO. : 5,374,254

DATED : December 20, 1994

INVENTOR(S) : Shelley J. Buma

It is certified that error appears in the above-identified patent and that said Letters Patent is hereby corrected as shown below:

In column 6, line 53, please delete "pod-side", and insert in lieu thereof --port-side--.

In column 6, line 54, please delete "top-pod", and insert in lieu thereof --top-port--.

In column 6, line 65, please delete "side-pod", and insert in lieu thereof --side-port--.

In column 6, line 66, please delete "top-pod", and insert in lieu thereof --top-port--.

In column 7, line 1, please delete "side-pod", and insert in lieu thereof --side-port--.

In column 7, line 12, please delete "side-pod", and insert in lieu thereof --side-port--.

In column 7, line 14, please delete "side-pod", and insert in lieu thereof --side-port--.

In column 8, line 15, please delete "pod", and insert in lieu thereof --port--.

In column 8, line 19, please delete "pod", and insert in lieu thereof --port--.

In column 8, line 19, please delete "top-pod", and insert in lieu thereof --top-port--.

In column 8, line 27, please delete "side-pod", and insert in lieu thereof --side-port--.

UNITED STATES PATENT AND TRADEMARK OFFICE
CERTIFICATE OF CORRECTION

PATENT NO. : 5,374,254
DATED : December 20, 1994
INVENTOR(S) : Shelley J. Buma

It is certified that error appears in the above-indentified patent and that said Letters Patent is hereby corrected as shown below:

Column 8, line 32, delete "top-pod", and insert in lieu thereof —top-port—.

Signed and Sealed this

Second Day of January, 1996

BRUCE LEHMAN

*Attest:*

*Attesting Officer*  Commissioner of Patents and Trademarks